United States Patent [19]

Watts

[11] 4,110,347
[45] Aug. 29, 1978

[54] CHROMAN DERIVATIVES

[75] Inventor: Eric Alfred Watts, Harlow, England

[73] Assignee: Beecham Group Limited, Great Britain

[21] Appl. No.: 757,353

[22] Filed: Jan. 6, 1977

Related U.S. Application Data

[62] Division of Ser. No. 577,614, May 14, 1975, Pat. No. 4,048,317.

[30] Foreign Application Priority Data

May 31, 1974 [GB] United Kingdom ............... 24348/74

[51] Int. Cl.$^2$ .................... C07D 311/02; A01K 31/35
[52] U.S. Cl. .................................................. 260/345.2
[58] Field of Search ....................................... 260/345.2

[56] References Cited

U.S. PATENT DOCUMENTS 3,923,836  12/1975  Bender et al. ..................... 260/345.2

Primary Examiner—Nicky Chan
Attorney, Agent, or Firm—Jacobs & Jacobs

[57] ABSTRACT

Anti-hypertensive derivatives of trans-3-hydroxy-4-amino-chroman, their preparation from amines and chroman epoxide derivatives, and pharmaceutical compositions containing such anti-hypertensive derivatives for reducing blood pressure in mammals, including humans.

18 Claims, No Drawings

CHROMAN DERIVATIVES

This is a division of Ser. No. 577,614 filed May 14, 1975, now U.S. Pat. No. 4,048,317.

The present invention relates to chroman derivatives, to a process for their preparation and to pharmaceutical compositions containing them.

More specifically, this invention relates to derivatives of trans-3-hydroxy-4-amino-chroman which possess blood pressure lowering activity, to their preparation by the reaction of amines on chroman epoxide derivatives and to pharmaceutical compositions containing the compounds of the invention which may be used in the treatment of hypertension in mammals including humans.

The compounds according to this invention are of the formula (I):

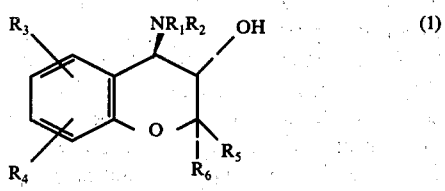

and acid addition salts thereof wherein $R_1$ is a hydrogen atom or a $C_{1-9}$ hydrocarbon group optionally substituted by a hydroxyl or $C_{1-6}$ alkoxyl group; $R_2$ is a hydrogen atom or $C_{1-6}$ alkyl group, or $NR_1; R_2$ is a 3–8 membered heterocyclic group optionally substituted by one or two methyl groups; $R_3$ is a hydrogen or halogen atom or a $C_{1-6}$ alkyl, $C_{2-6}$ alkenyl, $C_{1-6}$ alkoxy, $C_{2-6}$ alkenoxyl, $C_{1-6}$ alkylthio, hydroxyl, amino, $C_{1-6}$ alkylamino, $C_{1-6}$ dialkylamino, nitro, trifluoromethyl, $C_{2-7}$ acylamino, $C_{1-6}$ alkoxysulphonylamino, carboxyl, nitrile or $AOR_7$, $ASR_7$, $ASO_2R_7$, $ANHR_7$, $ANR_7COR_8$, $ANR_7SO_2R_8$ or $ANR_7CO_2R_8$ group wherein A is an alkylene group of 1–4 carbon atoms, $R_7$ is an alkyl group of 1–4 carbon atoms and $R_8$ is an alkyl group of 1–4 carbon atoms; $R_4$ is a hydrogen or halogen atom or methyl or methoxy, or $R_3$ together with $R_4$ forms a —CH=CH—CH=CH—, —NH—CH=CH—, —CH$_2$—CH$_2$—CH$_2$—CH$_2$— or —CH$_2$—CH$_2$—CH$_2$—CO— system; $R_5$ is a hydrogen atom or a $C_{1-6}$ alkyl or phenyl group; and $R_6$ is a hydrogen atom or a $C_{1-6}$ alkyl or phenyl group.

Suitable groups $R_1$ include the hydrogen atom and the methyl, ethyl, n-propyl, iso-propyl, n-butyl, iso-butyl, sec-butyl, t-butyl, n-pentyl, iso-pentyl, hexyl, allyl, phenyl, benzyl, tolyl, cyclopropylmethyl, cyclohexyl and the like groups.

Particularly suitable groups $R_1$ include $C_{1-6}$ alkyl groups.

Suitable groups $R_2$ include the hydrogen atom and the methyl, ethyl, propyl and like groups.

Suitable heterocyclic groups $NR_1R_2$ include the pyrrolidyol, piperidyl, morpholino, methylpyrrolidyl, N-methylpiperazine, hexamethyleneamino, N-phenylpiperazine, hexamethylenetetramine and the like groups.

Especially suitable groups $R_5$ and $R_6$ include the methyl and ethyl groups.

Preferred groups $R_5$ and $R_6$ include the methyl group.

Particularly suitable compounds of the formula (I) wherein $R_4$ is a hydrogen atom include those of the formula (II):

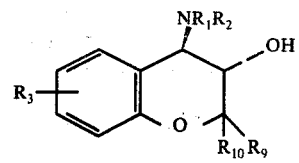

and their salts wherein $R_3$ is as defined in relation to formula (I), $R_9$ is a methyl or ethyl group, $R_{10}$ is a methyl or ethyl group and either (a), $NR_1R_2$ is a group $NR_{11}R_{12}$ wherein $R_{11}$ is an alkyl group of 1–4 carbon atoms and $R_{12}$ is a hydrogen atom or a methyl or ethyl group or (b) $NR_1R_2$ is a group of the sub-formula:

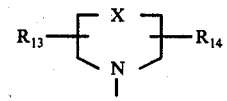

wherein X is a bond joining the two carbon atoms or is a CH$_2$, CH$_2$.CH$_2$, CH$_2$.CH$_2$.CH$_2$, CH:CH, O, S or NCH$_3$ group, $R_{13}$ is a hydrogen atom or a methyl group and $R_{14}$ is a hydrogen atom or a methyl group.

Most suitably, $NR_{11}R_{12}$ is a N(CH$_3$)$_2$ or NH C$_{1-4}$ alkyl group.

Most suitably X is a bond or a CH$_2$ or CH$_2$CH$_2$ group.

Particularly suitable groups $R_3$ for inclusion in compounds of the formula (I) or (II) include the allyl, allyloxy, nitro, trifluoromethyl, nitrile, NH.CO.$R_{16}$, NHSO$_2R_{16}$, NHSO$_3R_{16}$, (CH$_2$)$_n$OR$_{16}$ or (CH$_2$)$_n$NH.CO.$R_{16}$ where $R_{16}$ is an alkyl group of 1–4 carbon atoms and n is 1, 2 or 3.

A further particularly suitable group of compounds of the formula (I) is that of the formula (III):

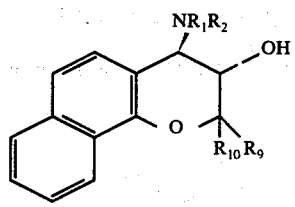

and salts thereof wherein $NR_1R_2$, $R_9$ and $R_{10}$ are as defined in relation to formula (II).

Particularly suitable groups $NR_1R_2$ in compounds of formulae (I), (II) or (III) include NHC(CH$_3$)$_3$, NH.CH(CH$_3$)$_2$, pyrrolidyl and piperidyl groups.

Particularly suitable groups $R_5$, $R_6$, $R_9$ and $R_{10}$ for inclusion in compounds of formulae (I), (II) or (III) include the methyl group.

One suitable sub-group of the compounds of formula (I) are those of formula (IV):

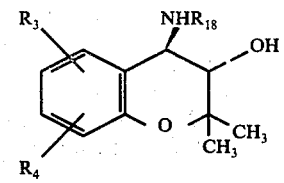

and salts thereof wherein $R_{18}$ is a $C_{1-6}$ alkyl, phenyl or benzyl group and $R_3$ and $R_4$ are as defined in relation to formula (I).

Most suitably $R_{18}$ is an iso-propyl, iso-butyl or t-butyl group.

A further sub-group of the compounds of formula (I) worthy of mention are those of formula (V):

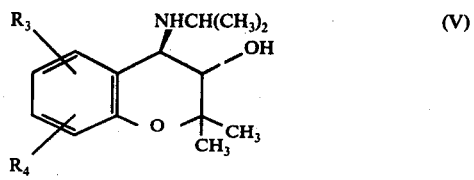

(V)

and salts thereof wherein $R_3$ and $R_4$ are as defined in relation to formula (I).

Suitable groups $R_3$ for inclusion in the compounds of formulae (II), (IV) or (V) include the hydrogen, fluorine, chlorine and bromine atoms and the methyl, ethyl, propyl, allyl, trifluoromethyl, methoxyl, methylthio, hydroxyl, nitro, allyloxyl, amino, acetamido, methoxysulphonylamino and the like groups.

Suitable groups $R_4$ for inclusion in the compounds of formulae (I), (IV) or (V) include the hydrogen, fluorine and chlorine atoms and the methyl and methoxyl groups.

Particularly suitable groups $R_3$ for inclusion in the compounds of the formula (II), (IV) or (V) include the hydrogen, fluorine and chlorine atoms and the methyl, trifluoromethyl, allyl, nitro, amino, acetamido, allyloxyl and methoxysulphonylamino groups.

Particularly suitable groups $R_4$ for inclusion in the compounds of the formulae (I), (IV) or (V) include the hydrogen and chlorine atoms, the hydrogen atom being preferred.

Further suitable values for $R_3$ for inclusion in the compounds of the formulae (II), (IV) or (V) are $(CH_2)_nOR_{19}$, $(CH_2)_nSR_{19}$, $(CH_2)_nSO_2R_{19}$, $(CH_2)_nNHCOR_{19}$, $(CH_2)_nNHCO_2R_{19}$ and $(CH_2)_nN(CH_3)COR_{19}$ groups wherein n is 1, 2 or 3 and $R_{19}$ is a methyl or ethyl group.

Compounds having vasodilatory activity may be found within formula (VI):

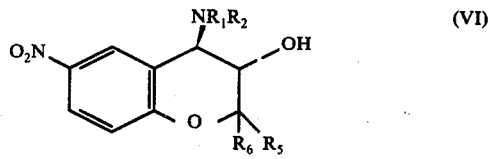

(VI)

and salts thereof wherein $R_1$, $R_2$, $R_5$ and $R_6$ are as defined in relation to formula (I).

Most suitably, $NR_1R_2$ is a cyclic group of sub-formula (b) as defined in relation to formula (II).

Most suitably, $R_5$ is a methyl or ethyl group and $R_6$ is a methyl or ethyl group.

Preferably $R_5$ and $R_6$ are both methyl groups.

Acid addition salts of the amino compounds of formulae (I) – (VI) may be made with acids in conventional manner. Suitable salt-forming acids include hydrochloric, hydrobromic, sulphuric, phosphoric, methanesulphonic, p-toluenesulphonic, acetic, propionic, succinic, citric, tartaric, mandelic, lactic, gluconic or other pharmaceutically acceptable organic or inorganic acid.

The compounds of the invention exist in optically active forms. Those skilled in the chemical arts will realise that racemic mixtures of amino compounds can often be separated into pure optical isomers using such techniques as fractional crystallisation with optically active acids and the like.

The compounds of formula (I) may be prepared by the reaction of an amine of the formula $NHR_1R_2$ with an epoxide of the formula (VII):

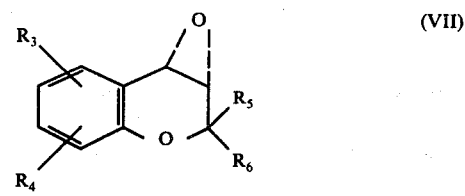

(VII)

wherein $R_3$, $R_4$, $R_5$ and $R_6$ are as defined in relation to formula (I).

The reaction of the amine and epoxide may be carried out at any non-extreme low, medium or high temperature (for example, $-10°$ C to $200°$ C) but in general ambient or slightly elevated temperatures are most suitable (for example, $12°$ C to $100°$ C). The reaction is normally carried out in the presence of a solvent such as alkanolic or ketonic solvent (for example, methanol, ethanol, propanol, acetone or methylethylketone).

It has been found that the reaction frequently proceeds smoothly and efficiently if the reaction is carried out in warmed or refluxing ethanol.

The above reaction has been found to give a trans product substantially free from the cis-isomer.

Compounds of formula (I) wherein $R_3$ is an amino group or substituted amino group may also be prepared by reduction (and optionally thereafter acylation or sulphonation) of the corresponding compound in which $R_3$ is a nitro group. Similarly, hydroxyl groups may be alkylated by conventional methods under conventional conditions if desired.

Frequently, pure compounds of this invention prepared by the preceding method may form crystals which contain water of crystallisation, for example, from 1 to 4 molecules of water per compound of formula (I).

The useful intermediates of the formula (VII) may be prepared by the method of Livingstone, R; (J.Chem.-Soc., 76 (1962)).

This method is summarised by reaction sequence A.

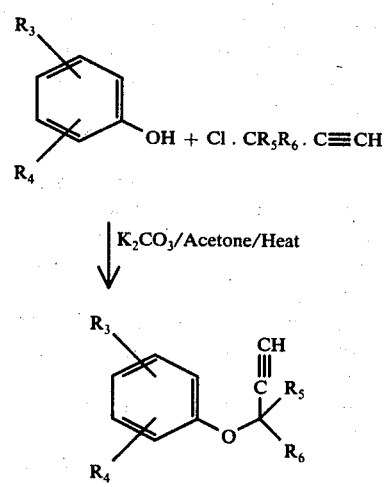

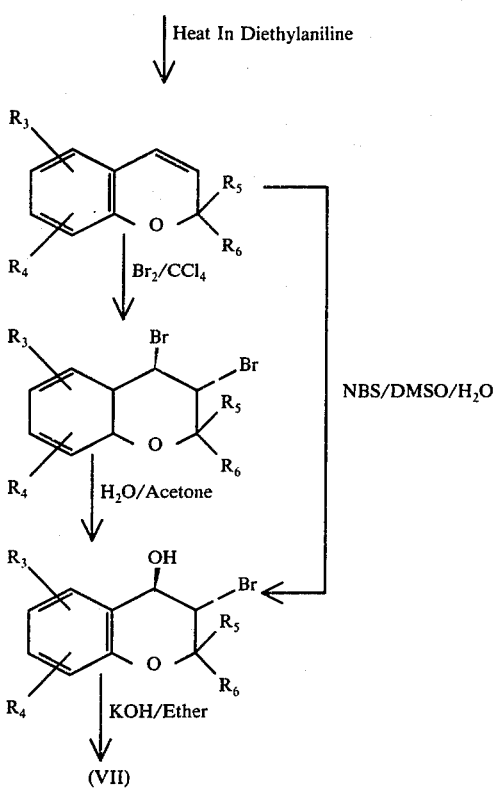

If necessary, the groups $R_3$ and/or $R_4$ may be protected during the above reaction sequence or may be transformed after the above reactions. For example, a compound of the formula (VII) in which $R_3$ is a hydroxyl group may be converted to the corresponding compound in which $R_3$ is an allyloxyl group by reaction with allyl bromide or the like or a compound of the formula (VII) wherein $R_3$ is an amine group may be converted into the corresponding compound wherein $R_3$ is an acetamido group by reaction with acetyl chloride or the like.

This invention also provides useful intermediates of the formula (VII) (a) wherein $R_3$ is a nitro group and $R_4$ is a hydrogen atom and (b) wherein $R_3$ together with $R_4$ forms a —CH = CH — CH = CH— residue.

A further aspect of this invention provides pharmaceutical compositions suitable for the treatment of hypertension. Such compositions may be suitable for parenteral or oral administration, but in general, oral compositions are preferred because of convenience of administration. Frequently, it is advantageous to administer compounds of the formula (VI) together with an adrenergic β-blocking agent.

The compositions of this invention are preferably in the form of unit dosage forms such as tablets or capsules. Such unit dosage forms will usually contain from 0.5 to 250 mg., for example, 2 to 100 mg., and will usually be administered from 1 to 6 times a day so that the daily dose for a 70 kg. human is from 2 to 250 mg., for example, 10 to 100 mg.

The compositions of this invention may be formulated in conventional manner, for example, in a manner similar to that used for known antihypertensive agents such as α-methyldopa, propranalol, guanethidine and the like. In conventional manner, the compositions of this invention may contain further active agents such as additional antihypertensive agents, diuretics and the like.

The following Examples are illustrative of the invention.

EXAMPLE 1

TRANS-4-ISOPROPYLAMINO-3,4-DIHYDRO-2,2-DIMETHYL-2H-BENZO [b]PYRAN-3-OL & ANALOGUES 3,4-Epoxy-3,4-dihydro-2,2-dimethyl-2H-benzo[b]pyran (10.00g.) prepared as described by R. Livingstone, J.Chem.Soc., 76, (1962), was treated with isopropylamine (12 ml: an excess) in refluxing ethanol (50 ml.) for 16 hours. The solution was then evaporated to dryness in vacuo to give an off-white solid (13.00g.). This residue was dissolved in diethyl ether and treated with ethereal hydrogen chloride to give a crystalline hydrochloride (12.06g). Re-crystallisation from ethanol/diethyl ether yielded trans-4-isopropyl-amino-3, 4-dihydro-2,2-dimethyl-2H-benzo[b]pyran-3-ol hydrochloride as colourless crystals, m.p. 172° – 174°. Similarly prepared were trans-4-dimethylamino-3,4-dihydro-2,2-dimethyl-2H-benzo[b] pyran-3-ol hydrochloride as colourless crystals m.p. 175° – 176°, trans-4-t-butylamino-3,4-dihydro-2,2-dimenthyl-2H-benzo[b] pyran-3-ol hydrochloride as colourless crystals m.p. 239°–241°, trans-4-morpholino-3,4-dihydro-2,2-dimethyl-2H-benzo[b]-pyran-3-ol hydrochloride m.p. 181°–187°.

EXAMPLE 2

TRANS-4-AMINO-3,4-DIHYDRO-2,2-DIMETHYL-2H-BENZO[b]PYRAN-3-OL HYDROCHLORIDE 3,4-Epoxy-3,4-dihydro-2,2-dimethyl-2H-benzo[b]pyran (3.00g.) and sodium azide (1.23g.; an excess) were refluxed in dioxane (25 ml.) and water (5 ml.) mixture for 24 hours. Dilution with water and extraction via diethyl ether gave trans-4-azido-3,4-dihydro-2,2-dimethyl-2H-benzo[b]-pyran-3-ol (3.06 g.) as needles from 60°–80° petroleum ether m.p. 70°°– 71°. To a solution of the hydroxy azide (2.90g.) in acetone (50 ml.) containing concentrated hydrochloric acid (10 ml.) was added with stirring and in portions, zinc dust (10 g.). Stirring was continued until gas evolution ceased. The zinc was filtered and washed with acetone. The combined washings and filtrate were diluted with water and extracted with diethyl ether. Basification of the aqueous layer and isolation via diethyl ether gave trans-4-amino-3,4-dihydro-2,2-dimethyl-2H-benzo[b]pyran-3-ol (2.70 g.), re-crystallised from ethanol m.p. 138°. Treatment with anhydrous hydrochloric acid as in Example 1 yielded trans-4-amino-3,4-dihydro-2,2-dimethyl-2H-benzo[b]pyran-3-ol hydrochloride, m.p. 223°–225°.

EXAMPLE 3

TRANS-4-ISOPROPYLAMINO-3,4-DIHYDRO-2,2-DIMETHYL-2H-NAPHTHO [1.2-b]PYRAN-3-OL & ANALOGUES 2,2-Dimethyl-2H-naphtho[1,2-b]pyran (18.92 g., prepared via reaction between sodium 1-naphthoxide and 3-chloro-3-methylbutyne in refluxing toluene) was treated with bromine (14.42 g.) in carbon tetrachloride (300 ml.) at ambient temperature. Removal of solvent in vacuo gave trans-3,4-dibromo-3,4-dihydro-2,2-dimethyl-2H-naphtho[1,2-b]pyran as a viscous oil (38.00 g.). This oil was dissolved in 400 ml. of a 2:1 mixture of acetone-water and refluxed for 17 hours. Isolation through diethyl-ether yielded trans-3-bromo-3,4-dihydro-2,2-dimethyl-2H-naphtho[1,2-b]pyran-4-ol as a viscous oil (25.00 g.). This crude bromohydrin was dissolved in diethyl-ether (200 ml.), potassium hydroxide flakes (25.00g.) were added and the mixture was stirred for 3 days at ambient temperature. Filtration and removal of solvent in vacuo gave crude expoxide, which was crystallised from 40°-60° petroleum-ether to yield 3,4-epoxy-3,4-dihydro-2,2-dimethyl-2H-naphtho[1,2-b]pyran (9.29 g.) as pale-yellow crystals, m.p. 120°-121°. Treatment of this epoxide (2.72g.) with isopropylamine (1.77g., an excess) in refluxing ethanol (30 ml.) for 24 hours, followed by removal of solvent, gave a brown gum (3.37g.) This residue was dissolved in acetone and treated with D-(+)-tartaric acid (1.77 g.). The acetone was evaporated to yield the crude salt (5.14 g.), which was recrystallised from acetone/ether to give trans-4-isopropyl-amino-3,4-dihydro-2,2-dimethyl-2H-naphtho[1,2-b]pyran-3-ol D-(+)-hydrogen tartrate as a hemihydrate (2.75 g.) m.p. 107° - 114°.

Similarly prepared was trans-4-pyrrolidino-3,4-dihydro-2,2-dimethyl-2H-naptho[1,2-b]pyran-3-ol D-(+)-hydrogen tartrate as a hydrate m.p. greater than 340°.

EXAMPLE 4

TRANS-4-ISOPROPYLAMINO-3,4-DIHYDRO-2H-NAPHTHO[1,2-b]PYRAN-3-OL

2H-Naphtho[1,2-b]pyran (4.00 g., prepared via cyclisation of 1-naphthyl propargyl ether in diethylaniline at 210°) was converted, via the same route as that described in Example 3, to 3,4-epoxy-3,4-dihydro-2H-naphtho[1,2-b]pyran (1.44 g.) m.p. 96°-99°. This epoxide (1.40g.) was treated with isopropylamine (1.00g., an excess) in refluxing ethanol (100 ml.) for 24 hours. Work-up as described in Example 4 yielded trans-4-isopropylamino-3,4-dihydro-2H-naphtho[1,2-b]pyran-3-ol D-(+)-hydrogen tartrate hydrate (0.30 g.) m.p. 108° - 110°.

EXAMPLE 5

TRANS-4-ISOPROPYLAMINO-3,4-DIHYDRO-2,2-DIMETHYL-6-NITRO-2H-BENZO[b]PYRAN-3-OL & ANALOGUES 2,2-Dimethyl-6-nitro-2H-benzo[b]pyran (5.18 g., prepared via cyclisation of 3-(p-nitrophenoxy)-3-methylbutyne in diethylaniline at 220°) was treated with bromine (4.03 g.) in carbon tetrachloride (110 ml.) at ambient temperature. Removal of solvent in vacuo gave trans-3,4-dibromo-3,4-dihydro-2,2-dimethyl-6-nitro-2H-benzo[b]pyran as brown crystals (9.01 g.) m.p. 130° - 134°. This dibromide (8.85 g.) was refluxed in a mixture of acetone (80 ml.) and water (35 ml.) for 20 hours and isolation via ether extraction gave the crude bromohydrin, which was recrystallised from 60° - 80° petroleum-ether to yield trans-3-bromo-3,4-dihydro-2,2-dimethyl-6-nitro-2H-benzo[b]pyran-4-ol as fawn microcrystals (2.00 g.) m.p. 114° - 116°. [Alternatively, 2,2-dimethyl-6-nitro-2H-benzo[b]pyran (8.20 g.) dissolved in dimethyl sulphoxide (80 ml.) containing water (1.4 ml.) and cooled in ice-water was treated with freshly recrystallized N-bromosuccinimide (14.24 g.) added in one portion. Dilution with water and isolation via ethyl acetate gave the bromohydrin (11.3 g.)]. This bromohydrin (1.92 g.) was stirred with potassium hydroxide pellets (1.92 g.) in diethyl-ether (50 ml.) for 4 days. Filtration and removal of solvent yielded 3,4-epoxy-3,4-dihydro-2,2-dimethyl-6-nitro-2H-benzo[b]pyran as a cream solid (1.33 g.) m.p. 91° - 93°. Treatment of this epoxide (1.14 g.) with isopropylamine (0.59 g., an excess) in refluxing ethanol (50 ml.) for 18 hours, followed by work-up as described in Example 1, gave trans-4-isopropylamino-3,4-dihydro-2,2-dimethyl-6-nitro-2H-benzo[b]pyran-3-ol hydrochloride (1.37 g.) m.p. 253° - 257°.

Similarly prepared were trans-4-methylamino-3,4-dihydro-2,2-dimethyl-6-nitro-2H-benzo[b]pyran-3-ol hydrochloride m.p. 296° - 299°, trans-4-dimethylamino-3,4-dihydro-2,2-dimethyl-6-nitro-2H-benzo[b]pyran-3-ol hydrochloride m.p. 260° - 261°, trans-4-diethylamino-3,4-dihydro-2,2-dimethyl-6-nitro-2H-benzo[b]pyran-3-ol hydrochloride m.p. 198° - 204°, trans-4-ethanolamino-3,4-dihydro-2,2-dimethyl-6-nitro-2H-benzo[b]pyran-3-ol hydrochloride m.p. 264° - 267°, trans-4-cyclopropylmethylamino-3,4-dihydro-2,2-dimethyl-6-nitro-2H-benzo[b]pyran-3-ol hydrochloride m.p. 256° - 259°, trans-4-tert.Butylamino-3,4-dihydro-2,2-dimethyl-6-nitro-2H-benzo[b]pyran-3-ol hydrochloride m.p 280°, trans-4-pyrrolidino-3,4-dihydro-2,2-dimethyl-6-nitro-2H-[b]pyran-3-ol hydrochloride m.p. 238° - 243°, trans-4-morpholino-3,4-dihydro-2,2-dimethyl-6-nitro-2H-benzo[b]pyran-3-ol hydrochloride m.p 243° - 248°, trans-4-piperidino-3,4-dihydro-2,2-dimethyl-6-nitro-2H-benzo[b]pyran-3-ol hydrochloride m.p. 240° - 245°, trans-4-[4-methylpiperidino]-3,4-dihydro-2,2-dimethyl-6-nitro-2H-benzo[b]pyran-3-ol hydrochloride m.p. 226° - 230°, trans-4-hexamethylenimino-3,4-dihydro-2,2-dimethyl-6-nitro-2H-benzo[b]pyran-3-ol hydrochloride m.p. 215° - 220°, trans-4-heptamethylenimino-3,4-dihydro-2,2-dimethyl-6-nitro-2H-benzo[b]pyran-3-ol hydrochloride m.p. 214° - 220°, trans-4-N-phenylpiperazino-3,4-dihydro-2,2-dimethyl-6-nitro-2H-benzo[b]pyran-3-ol dihydrochloride m.p. 147° - 188°, trans-4-[2,5-dimethylpyrrolidino]-3,4-dihydro-2,2-dimethyl-6-nitro-2H-benzo[b]pyran-3-ol hydrochloride m.p. 158° - 206°.

EXAMPLE 6

TRANS-4-ISOPROPYLAMINO-3,4-DIHYDRO-2,2-DIMETHYL-6-AMINO-2H-BENZO[b]PYRAN-3-OL SULPHATE

Trans-4-Isopropylamino-3,4-dihydro-2,2-dimethyl-6-nitro-2H-benzo[b]pyran-3-ol (3.54 g.) was added to a solution of stannous chloride (7.90 g.) in ethanol (36 ml.) and concentrated hydrochloric acid (60 ml.) and stirred for 3 hours at ambient temperature. After dilution, work-up via diethyl ether gave a gum (3.25 g.). Purification of this gum (2.00 g.) by application to silica gel plates and development with ethyl acetate/60°-80° petroleum ether mixture gave an amorphous solid (1.01 g.) which was dissolved in dilute sulphuric acid and evaporated to dryness to yield trans-4-isopropylamino-3,4-dihydro-2,2-dimethyl-6-amino-2H-benzo[b]pyran-3-ol sulphate as a light brown solid m.p. 180° - 190°.

EXAMPLE 7

TRANS-4-ISOPROPYLAMINO-3,4-DIHYDRO-2,2-DIMETHYL-6-ACETAMIDO-2H-BENZO[b]PYRAN-3-OL HYDROCHLORIDE 2,2-Dimethyl-6-acetamido-2H-benzo[b]pyran [(1.26 g.), prepared as described in British Patent No. 1,121,307] dissolved in dimethyl sulphoxide (20 ml.) containing water (0.2 ml.) and cooled in an ice-bath was treated with N-bromosuccinimide (2.20 g., an excess). Work-up as described in Example 6, gave a gum (1.46 g.) which was purified by application to silica gel plates and developed with ethyl acetate - 60°-80° petroleum ether mixtures gave pale yellow crystals (0.96 g.) from ethylacetate acetate/60°-80° petroleum ether of trans-3-bromo-3,4-dihydro-2,2-dimethyl-6-acetamido-2H-benzo[b]pyran-4-ol m.p. 170°. The bromohydrin (0.92 g.) was stirred with potassium hydroxide pellets (1.50 g.) in diethyl ether (120 ml.) for 4.5 days. Filtration and removal of solvent gave 3,4-epoxy-3,4-dihydro-2,2-dimethyl-6-acetamido-2H-benzo[b]pyran (0.55 g.) recrystallised from ethyl acetate 60°-80° petroleum ether as colourless needles m.p. 173° - 175°. Treatment of this epoxide (0.50 g.) with isopropylamine (1.5 g., an excess) and work-up as in Example 1, gave trans-4-isopropylamino-3,4-dihydro-2,2-dimethyl-6-acetamido-2H-benzo[b]pyran-3-ol hydrochloride (0.38 g.) m.p. 259°-260° from diethyl ether ethanol.

EXAMPLE 8

TRANS-4-ISOPROPYLAMINO-3,4-DIHYDRO-2,2-DIETHYL-2H-BENZO[b]PYRAN-3-OL HYDROCHLORIDE 2,2-Diethyl-2H-benzo[b]pyran (3.86 g.) was treated with N-bromosuccinimide (7.40 g.) under the conditions described in Example 5 yielding trans-3-bromo-3,4-dihydro-2,2-diethyl-2H-benzo[b]pyran-4-ol (5.70 g.), as a pale yellow solid m.p. 75° - 77° after trituration with 60°-80° petroleum ether. Reaction of this bromohydrin (5.60 g.) with potassium hydroxide pellets (6.38 g.) in diethyl ether (300 ml.) for 4.5 days following Example 7 gave 3,4-epoxy-3,4-dihydro-2,2-diethyl-2H-benzo[b]pyran as a colourless liquid (4.28 g.) displaying signals centred at δ 3.66 and 3.78 (doublets, of coupling constant J = 4Hz) in its p.m.r. spectrum ($CDCl_3$, with TMS as internal standard) corresponding to protons located at C-3 and C-4. Treatment of this epoxide (1.40 g.) with isopropylamine (3.50 g., an excess) and work-up as in Example 1, gave trans-4-isopropylamino-3,4-dihydro-2,2-diethyl-2H-benzo[b]pyran-3-ol hydrochloride (1.67 g.) m.p. 200° - 202°.

A similar preparation gave trans-4-pyrrolidino-3,4-dihydro-2,2-diethyl-2H-benzo[b]pyran-3-ol hydrochloride m.p. 133°-138°.

EXAMPLE 9

PHARMACOLOGY

Compounds of formula (I):

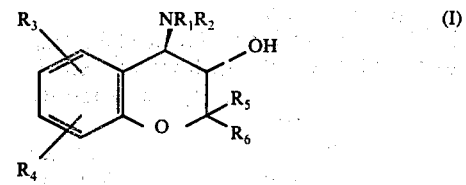

and certain standard compounds were tested in DOCA treated hypertensive rats. The results obtained 6 hours after oral administration at a dose of 100 mg/kg of compound are shown in Table 1.

TABLE I

| $R_1$ | $R_2$ | $R_3$ | $R_4$ | $R_5$ | $R_6$ | Salt | Approximate % Change In Systolic Blood Pressure |
|---|---|---|---|---|---|---|---|
| $CH(CH_3)_2$ | H | CH=CH—CH=CH | H | $CH_3$ | $CH_3$ | Tartrate | −13 |
| $CH(CH_3)_2$ | H | 6-$NO_2$ | H | $CH_3$ | $CH_3$ | HCl | −20 |
| — | $(CH_2)_5$— | 6-$NO_2$ | H | $CH_3$ | $CH_3$ | HCl | −56 |
| $C_2H_5$ | $C_2H_5$ | 6-$NO_2$ | H | $CH_3$ | $CH_2$ | HCl | −22 |
| $(CH_2)_4$ | — | 6-$NO_2$ | H | $CH_3$ | $CH_3$ | HCl | −66 |
| $CH(CH_3)_2$ | H | H | H | $C_2H_5$ | $C_2H_5$ | HCl | −16 |
| dl practalol | | | | | | | −3 |
| dl pindolol | | | | | | | −10 |
| α-methyldopa | | | | | | | −24 |

What we claim is:
1. A compound of the formula

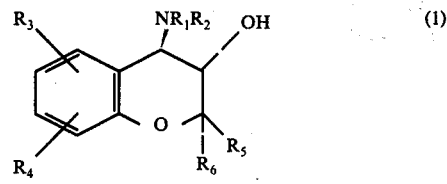

or a pharmaceutically acceptable acid addition salt thereof wherein
   $R_1$ is hydrogen or a hydrocarbon of 1 to 9 carbon atoms unsubstituted or substituted by hydroxyl or alkoxyl of 1 to 6 carbon atoms;
   $R_2$ is hydrogen or alkyl of 1 to 6 carbon atoms;
   $R_3$ together with $R_4$ form a —CH=CH—CH=CH— or —$CH_2$—$CH_2$—$CH_2$—$CH_2$— ring system;
   $R_5$ is hydrogen, alkyl of 1 to 6 carbon atoms or phenyl; and
   $R_6$ is hydrogen, alkyl of 1 to 6 carbon atoms or phenyl.

2. A compound according to claim 1 wherein $R_1$ is alkyl of 1 to 6 carbon atoms and $R_2$ is hydrogen or alkyl of 1 to 3 carbon atoms.

3. A compound according to claim 1 wherein the compound is of the formula (IV):

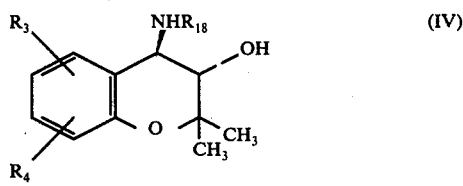

or a pharmaceutically acceptable acid addition salt thereof wherein
   $R_{18}$ is of 1 to 6 carbon atoms, phenyl or benzyl; and
   $R_3$ together with $R_4$ form a —CH=CH—CH=CH— or —$CH_2$—$CH_2$—$CH_2$—$CH_2$— ring system.

4. A compound according to claim 3 wherein $R_{18}$ is isopropyl, isobutyl or t-butyl.

5. The compound according to claim 1 which is trans-4-isopropylamino-3,4-dihydro-2,2-dimethyl-2H-naphtho-[1,2-b]pyran-3-ol or a pharmaceutically acceptable addition salt thereof.

6. The compound according to claim 1 which is trans-4-tertiarylbutylamine-3,4-dihydro-2,2-dimethyl-2H-naphtho-[1,2-b]pyran-3-ol or a pharmaceutically acceptable acid addition salt thereof.

7. A compound according to claim 1 wherein $R_5$ and $R_6$ are each methyl.

8. A compound according to claim 1 of the formula (III):

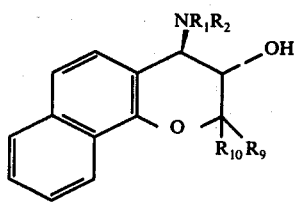

or a pharmaceutically acceptable acid addition salt thereof wherein $NR_1R_2$ is a moiety $NR_{11}R_{12}$ wherein $R_{11}$ is alkyl of 1 to 4 carbon atoms and $R_{12}$ is hydrogen, methyl or ethyl;

$R_9$ is methyl or ethyl; and $R_{10}$ is methyl or ethyl.

9. A compound according to claim 1 in the form of an acid addition salt wherein said salt is selected from the group consisting of the hydrochloride, hydrobromide, sulphate, phosphate, methane sulfonate, p-toluene sulfonate, acetate, propionate, succinate, citrate, tartrate, mandelate, lactate or gluconate.

10. A compound according to claim 1 wherein
$R_1$ is hydrogen, methyl, ethyl, n-propyl, isopropyl, n-butyl, isobutyl, sec-butyl, t-butyl, n-pentyl, isopentyl, hexyl, allyl, phenyl, benzyl, tolyl, cyclopropylmethyl, or cyclohexyl.

11. A compound according to claim 1 wherein
$R_1$ is alkyl of 1 to 6 carbon atoms.

12. A compound according to claim 1 wherein
$R_2$ is hydrogen, methyl, ethyl or propyl.

13. A compound according to claim 1 wherein
$R_5$ and $R_6$ are each methyl or ethyl.

14. A compound according to claim 8 wherein the moiety $NR_{11}R_{12}$ is a $N(CH_3)_2$ or NH-alkyl of 1 to 4 carbon atoms in the alkyl moiety.

15. A compound according to claim 1 wherein the moiety $NR_1R_2$ is $NHC(CH_3)_3$ or $NH-CH(CH_3)_2$.

16. The compound according to claim 1 which is trans-4-isopropylamino-3,4-dihydro-2,2-dimethyl-2H-naphtho[1,2-b]pyran-3-ol D-(+)-hydrogen tartrate.

17. The compound according to claim 1 which is trans-4-isopropylamino-3,4-dihydro-2H-naphtho[1,2b]-pyran-3-ol D-(+)-hydrogen tartrate hydrate.

18. A compound according to claim 8 wherein $R_9$ and $R_{10}$ are each methyl.

* * * * *